(12) United States Patent
Krueger

(10) Patent No.: US 9,297,866 B2
(45) Date of Patent: Mar. 29, 2016

(54) GENERAL INDUCTIVE HANDPIECE FOR ACTIVE DEVICES

(75) Inventor: Sascha Krueger, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 403 days.

(21) Appl. No.: 13/141,092

(22) PCT Filed: Nov. 23, 2009

(86) PCT No.: PCT/IB2009/055294
§ 371 (c)(1),
(2), (4) Date: Jun. 21, 2011

(87) PCT Pub. No.: WO2010/076681
PCT Pub. Date: Jul. 8, 2010

(65) Prior Publication Data
US 2011/0257511 A1    Oct. 20, 2011

Related U.S. Application Data

(60) Provisional application No. 61/141,937, filed on Dec. 31, 2008.

(51) Int. Cl.
*A61B 5/055* (2006.01)
*G01R 33/36* (2006.01)
*G01R 33/34* (2006.01)

(52) U.S. Cl.
CPC .......... *G01R 33/34084* (2013.01); *A61B 5/055* (2013.01); *G01R 33/3628* (2013.01)

(58) Field of Classification Search
CPC ........... G01R 33/3628; G01R 33/3642; G01R 33/34084; G01R 33/285; A61B 5/055; A61B 2018/00839; A61B 2019/5236; A61B 18/1492; A61N 2011/086
USPC .......................... 324/322; 600/411, 423, 424
See application file for complete search history.

(56) References Cited

U.S. PATENT DOCUMENTS 5,807,253 A    9/1998 Dumoulin et al.
5,849,020 A   12/1998 Long et al.
(Continued)

FOREIGN PATENT DOCUMENTS

| DE | 3708801 A1 | 3/1987 |
|----|------------|--------|
| EP | 0850595 A1 | 7/1998 |
| WO | 2006067703 A2 | 6/2006 |

OTHER PUBLICATIONS

By S. Weiss et al. "Transmission Line for Improved RF Safety of Interventional Devices"; Magnetic Resonance in Medicine, vol. 54 No. 1, (pp. 182-189) please see U.S. Pat. No. 7,750,637 B3; pp. 1-2.

*Primary Examiner* — Long V Le
*Assistant Examiner* — Helene Bor

(57) ABSTRACT

A handpiece defines a bore in which a proximal end of a catheter or other interventional instrument is received. An insulating support supports an interventional instrument which carries a transmission line winding in, but spaced from, the internal bore. A handpiece winding disposed along the bore interacts with the instrument transmission line winding to form an inductive coupling with the instrument transmission line winding. After the handpiece is slid axially to adjust the inductive coupling between the handpiece and windings, a locking mechanism functions in such a manner that the interventional instrument is inhibited from axial sliding motion relative to the handpiece while permitting rotation of the interventional instrument relative to the handpiece thus maintaining the inductive coupling while allowing optimal handling of the device.

13 Claims, 4 Drawing Sheets

(56) References Cited

U.S. PATENT DOCUMENTS

| | | | |
|---|---|---|---|
| 5,868,674 A * | 2/1999 | Glowinski et al. | 600/410 |
| 6,246,896 B1 | 6/2001 | Dumoulin et al. | |
| 6,606,513 B2 * | 8/2003 | Lardo et al. | 600/411 |
| 6,628,980 B2 * | 9/2003 | Atalar et al. | 600/423 |
| 7,064,549 B1 * | 6/2006 | Hudson | 324/318 |
| 7,750,637 B2 | 7/2010 | Weiss et al. | |
| 2001/0056232 A1 | 12/2001 | Lardo et al. | |
| 2002/0109503 A1 | 8/2002 | Kestler et al. | |
| 2003/0050557 A1 * | 3/2003 | Susil et al. | 600/424 |
| 2005/0218897 A1 | 10/2005 | Schulz et al. | |
| 2009/0062739 A1 * | 3/2009 | Anderson | 604/164.13 |

* cited by examiner

GENERAL INDUCTIVE HANDPIECE FOR ACTIVE DEVICES

CROSS REFERENCE TO RELATED APPLICATIONS

This application claims the benefit of U.S. provisional application Ser. No. 61/141,937 filed Dec. 31, 2008, which is incorporated herein by reference.

DESCRIPTION

The present application relates to the magnetic resonance arts, more particularly to a handpiece for receiving signals of at least one electrical interventional accessory suitable for use in a magnetic resonance system.

A magnetic resonance (MR) imaging system is used for the examination and treatment of patients. By such a system, the nuclear spins of the body tissue to be examined are aligned by a static main magnetic field $B_0$ and are excited by transverse magnetic fields $B_1$ oscillating in the radiofrequency band to induce resonance. The resulting resonance relaxation signals are exposed to gradient magnetic fields to localize the resultant resonance relaxation signals. The resonance relaxation signals are received and reconstructed into a single or multiple dimension image, for example.

A whole-body radiofrequency (RF) coil system provides the transmission of the $B_1$ RF signals and the reception of the resonances signals. In addition to the whole-body RF coil system which is permanently built into the imaging apparatus, use is also made of local or surface coils which can be flexibly arranged, for example, as a sleeve or pad around or in a specific region to be examined In some applications, interventional accessories, e.g., a catheter, are introduced into the patent during imaging. Catheters often have one or more RF coil elements which can be used for locating the catheter within the patient, receiving resonance signals from adjacent tissue, and the like.

Transmission lines or paths connect accessory devices like catheters, needles, imaging coils, guidewires, and the like with an active unit, such as a power supply, a receiving/transmission device, a control unit, or the like. Active units send RF pulses to the inserted device coils and/or receive RF signals from the inserted device coils. Typically, electrical connections to an active unit are required. To avoid the potential risk of electric currents unintentionally flowing into the patient and/or the operator, additional measures to ensure patient and operator safety are generally required.

When the interventional devices are guided through MR fields, particularly the $B_1$ RF fields can introduce common mode signals (currents) in the transmission line and in the surrounding body tissue. These currents involve not only the risk of disturbances or destruction of the interventional device and/or the active unit, but also these currents can give rise to substantial heating of the directly adjacent tissue resulting in potentially severe burns for the patient. A second major concern is that a malfunction in the active unit or an unintentional static build-up and discharge by the operator could send currents through the transmission lines into the subject.

The present application provides a new and improved MR inductive handpiece (holder) for active devices which overcomes the above-referenced problems and others.

In accordance with one aspect, a handpiece is configured to receive any of a variety of catheters or other interventional instruments. The handpiece includes an insulating support which supports a portion of the interventional instrument which carries a transmission line in, but spaced from, an internal bore of the handpiece. A handpiece winding is disposed along the bore and interacts with the transmission line to form an inductive coupling therebetween.

In accordance with another aspect, a magnetic resonance system includes a magnet which generates a static magnetic field in an examination region, a radio frequency transmit coil configured to induce magnetic resonance in the examination region, a radio frequency receive coil configured to acquire magnetic resonance data from the examination region, and a handpiece as discussed above.

In accordance with another aspect, a method of operating a catheter or other interventional instrument is provided. The interventional instrument is connected with the handpiece such that a transmission line extending through the interventional instrument is supported in and spaced from a bore of the handpiece and axially slidable relative to the bore and rotatable relative to the bore. The interventional instrument is slid axially relative to the bore to adjust an inductive coupling between an interventional instrument inductive winding connected to the transmission line and a handpiece inductive winding to adjust a coupling strength. The interventional instrument can be locked to inhibit axially sliding movement relative to the handpiece while permitting rotation of the interventional instrument relative to the handpiece, thus maintaining the coupling state and allowing free rotational movement of the device.

One advantage resides in reduced complexity and cost of the disposable part of the active interventional device (catheter, needle, guidewire).

Another advantage resides in possible use of a generic handpiece for multiple devices. The generic handpiece can be reuseable further reducing cost.

Another advantage resides in manual control of coupling strength yielding improved signal strength and signal-to-noise ratio.

Another advantage resides in improved rotational handling of the active device compared to devices with standard fixed handpieces.

Another advantage resides in improved patient safety due to the inductive (i.e. non-contact) connection.

Still further advantages of the present invention will be appreciated by those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention. FIG. 1 is a diagrammatic side view in partial section of an MR apparatus along with an inductive handpiece inductively couple to an interventional device;

Figure 1:
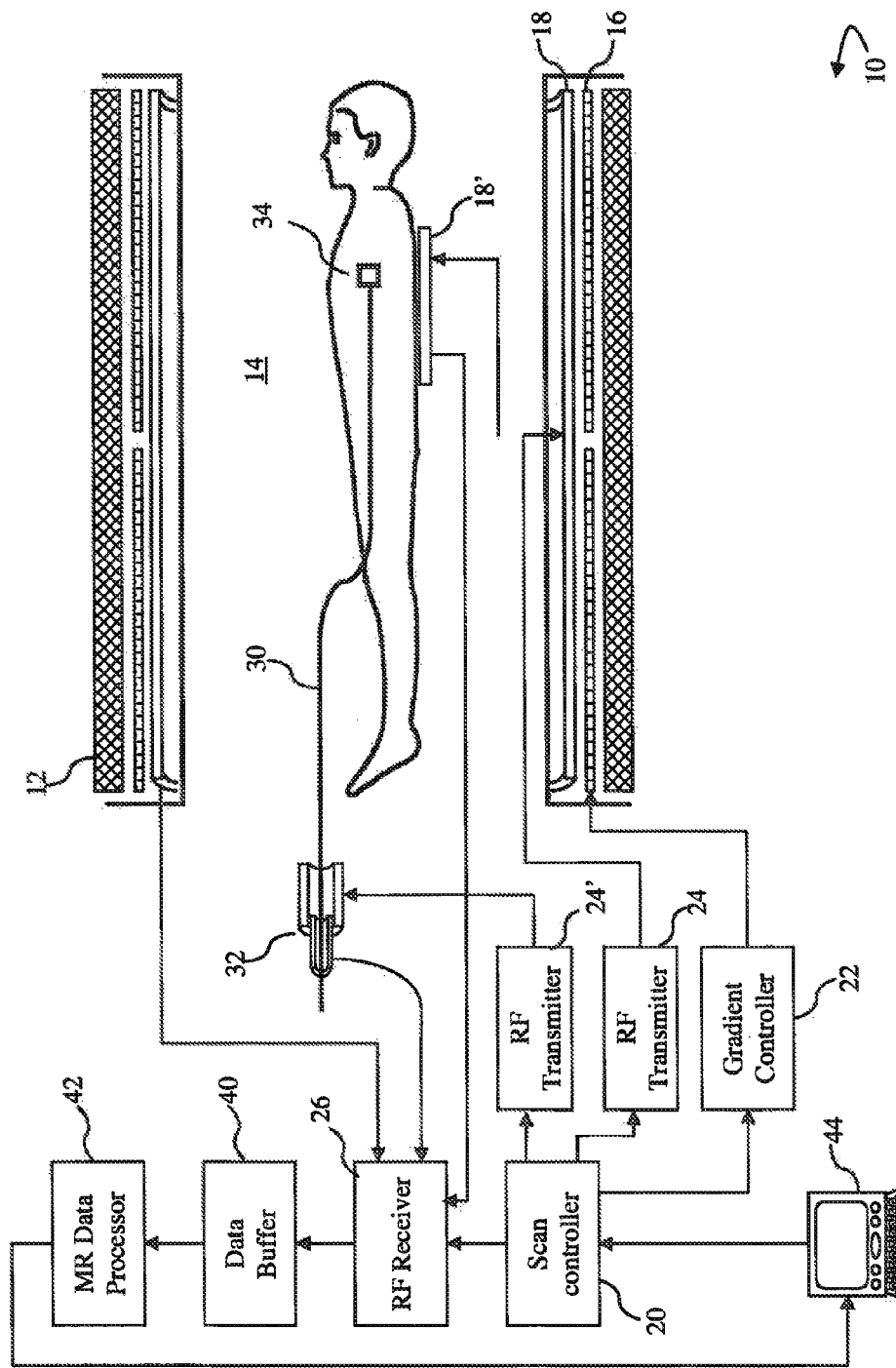

With reference to FIG. 1, a magnetic resonance imaging system 10 includes a main magnet 12 which generates a temporally uniform $B_0$ field through an examination region 14. The main magnet can be an annular or bore-type magnet, a C-shaped open magnet, other designs of open magnets, or the like. Gradient magnetic field coils 16 are disposed adjacent the $B_0$ magnet in order to generate magnetic field gradients in the examination region along selected axes relative to the $B_0$ magnetic field. A radio frequency (RF) coil, such as a whole-body radio frequency coil 18 is disposed adjacent the examination region. Optionally, local or surface RF coils 18' are provided in addition to or instead of the whole-body RF coil 18.

A scan controller 20 controls a gradient controller 22 which causes the gradient coils to apply selected magnetic field gradient pulses across the imaging region, as may be appropriate to a selected magnetic resonance imaging or spectroscopy sequence. The scan controller 20 also controls an RF transmitter 24 which causes the whole-body or local RF coils to generate magnetic resonance excitation and manipulation $B_1$ pulses. The scan controller also controls an RF receiver 26 which is connected to the whole-body or local RF coils to receive magnetic resonance signals therefrom.

An interventional instrument, such as a catheter 30, is removably connected with a handpiece 32 which is held by the surgeon or clinician. Various other types of interventional instruments and catheters are contemplated. For example, the catheter may include a guide wire, a stent, an injector, a needle, a passage for introducing contrast agents or other fluids, etc. The catheter or other interventional instrument, in the illustrated embodiment, has a distal coil 34 disposed at a distal end thereof. Optionally, additional coils may be disposed along the length of the catheter. Optionally, other electrical equipment such as an amplifier, matching and tuning circuitry, or other circuitry, may be disposed in the tip of the catheter adjacent the coil 34. The catheter, particularly electrical conductors therein, are inductively coupled, but not directly connected by electrical wires, via the handpiece 32 with the RF receiver 26 and/or an RF transmitter 24'. The RF transmitter 24' can be the same as the RF transmitter 24. Alternately, as illustrated in FIG. 1, the RF transmitters 24 and 24' can be different transmitters to facilitate the significantly different transmit power levels.

The interventional instrument coil 34 can be used in various ways. In one embodiment, RF resonance excitation and manipulation signals are applied via the RF transmitter 24' to the coil 34 to induce resonance in tissue closely adjacent the coil. In other embodiments, resonance is induced in the adjacent tissue by the whole-body RF coil 18 or a local RF coil 18' on the exterior of the patient. The coil 34 can also be used in a receive mode to receive resonance signals from resonating tissue adjacent the coil. Such resonance signals are sent to the RF receiver 26 to be processed analogous to other received magnetic resonance signals. In another mode, the coil 34 is used for locating the interventional instrument, particularly the distal tip of the catheter. Various localization techniques are known. Most commonly, MR sequences comprising one or more projection measurements in one or multiple linear independent directions are performed, which exploit the point-like signal distribution of coil 34 to reconstruct its position in one or more dimensions. In some localization techniques, the coil 34 is caused to switch between resonant and non-resonant configurations. In others, an RF signal at a different frequency from the Larmor frequency is applied to the coil 34. This locator RF signal can be received by the whole-body coil 18 or a local coil 18'. The magnetic field gradients can be applied for spatially localizing the locator RF signal in a separate location process or the localization of the coil can be processed concurrently with processing of the magnetic resonance signals. Various other electrical functions can also be performed in the interventional instrument.

The received data from the receiver 26 is temporarily stored in a data buffer 40 and processed by a magnetic resonance data processor 42. The magnetic resonance data processor can perform various functions as are known in the art, including image reconstruction, magnetic resonance spectroscopy, catheter or interventional instrument localization, and the like. Reconstructed magnetic resonance images, spectroscopy readouts, interventional instrument location information, and other processed MR data are displayed on a graphic user interface 44. The graphic user interface 44 also includes a user input device which a clinician can use for controlling the scan controller 20 to select scanning sequences and protocols, and the like.

Figure 2:
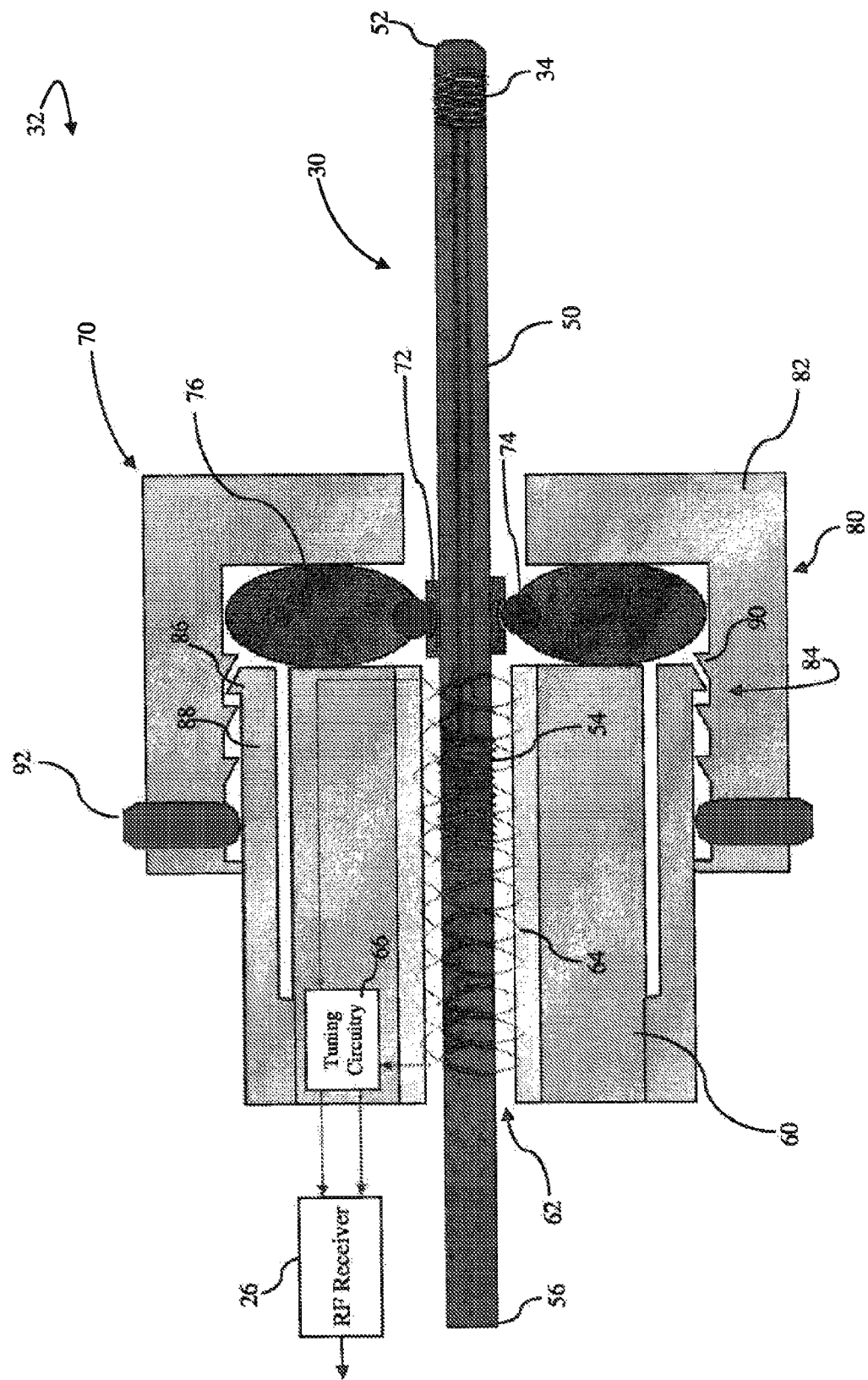
FIG. 2 is a diagrammatic side sectional view of an inductive handpiece inductively coupled to an interventional device.

With reference to FIG. 2, the RF coil 34 is connected with a transmission line 50 which extends the length of the catheter or other interventional instrument 30 from a distal end 52 to an interventional instrument inductive proximal winding 54 disposed adjacent a proximal end 56. Optionally, the transmission line can include inductive couplings, e.g., at quarter wavelength intervals, to block the transfer of direct currents, off-resonance frequency currents, and common-mode resonance. Additionally the interventional instrument maybe hermetically sealed.

The handpiece 32 includes a body portion 60 which defines a bore 62. The bore 62 is larger in diameter than at least the portion of the catheter or interventional instrument adjacent the proximal end 56 that includes the coil proximal 54. In this manner, the proximal end of the catheter can be received in, but spaced from the bore 62. A handpiece inductive coil 64 is disposed along the bore, e.g., wrapped annularly around it in a helical or sinusoidal manner. The interventional instrument transformer proximal winding 54 and the handpiece inductive winding 64 define a transformer which is tuned to pass appropriate frequency RF signals, e.g., resonance frequency signals, therebetween but are configured to block the passage of direct current and other frequencies. Optionally, electrical circuitry such as tuning circuitry 66 is mounted in the handpiece body, e.g., hermetically sealed into the handpiece body for easy cleaning and sterilization. The circuitry 66 may further include matching circuitry, analog-to-digital converters, amplifiers, and the like.

The interventional instrument is supported in an insulating support mechanism 70. The insulating support mechanism includes a bushing or bearing race 72 whose interior is sized such that the interventional instrument can be slid relative to the bushing 72 and can be rotated therein. By moving the interventional instrument axially, the relative position of the interventional instrument inductive winding 54 and the handpiece inductive winding 64 is selectively adjusted, which adjusts the coupling between these two windings of the transformer. By adjusting the coupling, the coupling strength, and hence the amplitude of the output signals from the coil 34, when it is functioning as an antenna, can be adjusted. Adjusting the coupling strength can make signals from the coil 34 adjacent the distal end of the interventional element brighter or less bright. The bushing 72, in turn, is supported by a bearing element 74, such as PTFE or rubber rolling bearings or an annular low friction ring. The bearing element 74, in turn, is supported by a compressible annular support element 76 such as a soft rubber ring.

A locking mechanism 80 which locks the interventional instrument against rotation includes a compression element 82 that selectively compresses the compressible, soft rubber ring 76 of the insulating support mechanism 70, squeezing the bearing elements 74 against the bushing 72. As the bushing 72 is compressed, it grips the interventional instrument to inhibit its axial sliding, while permitting rotation of the bushing 72 relative to the bearing element 74, i.e., rotation of the interventional instrument relative to the handpiece. In this manner, the interventional radiologist or other user can hold the handpiece body 32 in one hand and rotate and otherwise manipulate the interventional instrument 30 with the other hand.

The locking mechanism 80 further includes a ratchet mechanism 84 for holding the compressible element 76 in a selected state of compression. More specifically, pawls 86 on spring elements 88 extend outward to engage annular ratchet elements or teeth 90 on the compression element 82. Pressing the compression element 82 toward the handpiece body snaps the ratchet elements 90 progressively over the pawls 86, locking the interventional instrument progressively tighter. To release the locking mechanism, release elements 92 are compressed to bias the spring elements 88 and their pawls 86 away from the ratchet elements 90, allowing the compression element 82 to move axially as the compressible element 76 expands.

Figure 3:
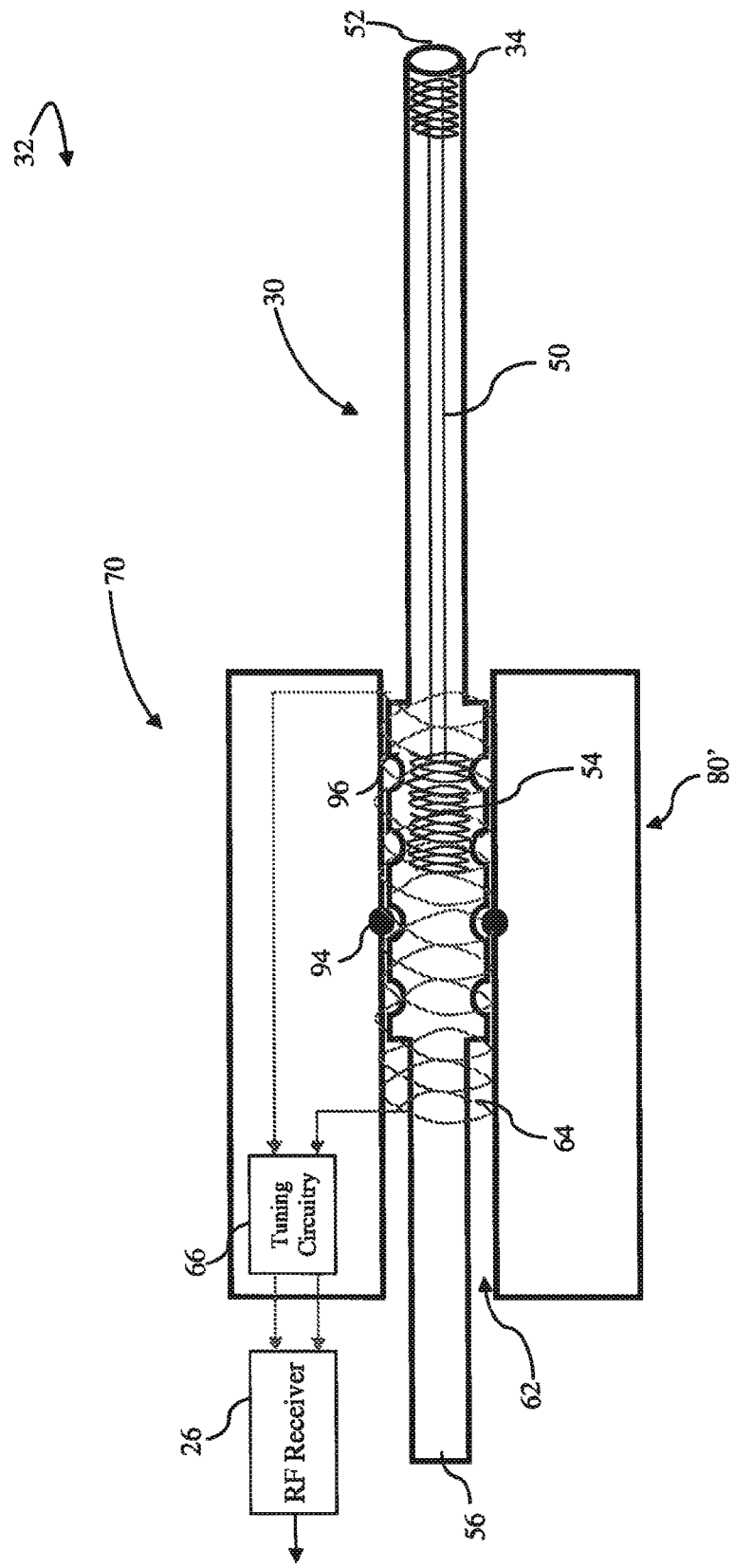
FIG. 3 is a diagrammatic side sectional view of an inductive handpiece inductively coupled to an interventional device employing an alternate locking mechanism.

With reference to FIG. 3, an alternate locking mechanism 80' includes an annular locking ring 94 within the bore 62' of the insulating support mechanism 70'. The locking ring is configured to resiliently engage an array of adjacent annular channels 96 of the interventional instrument. It should be appreciated that either the locking ring 94 or the channels 96 or both are made of a resilient material that allows the locking ring 94 to traverse the raised edges between adjacent channels 96. As the locking ring engages a channel, it rests in one of the channels inhibiting axial sliding while permitting rotation relative to the handpiece. In this manner, the interventional radiologist, technician or other user can hold the handpiece body 32' in one hand and rotate and otherwise manipulate the interventional instrument 30' with the other hand.

Figure 4:
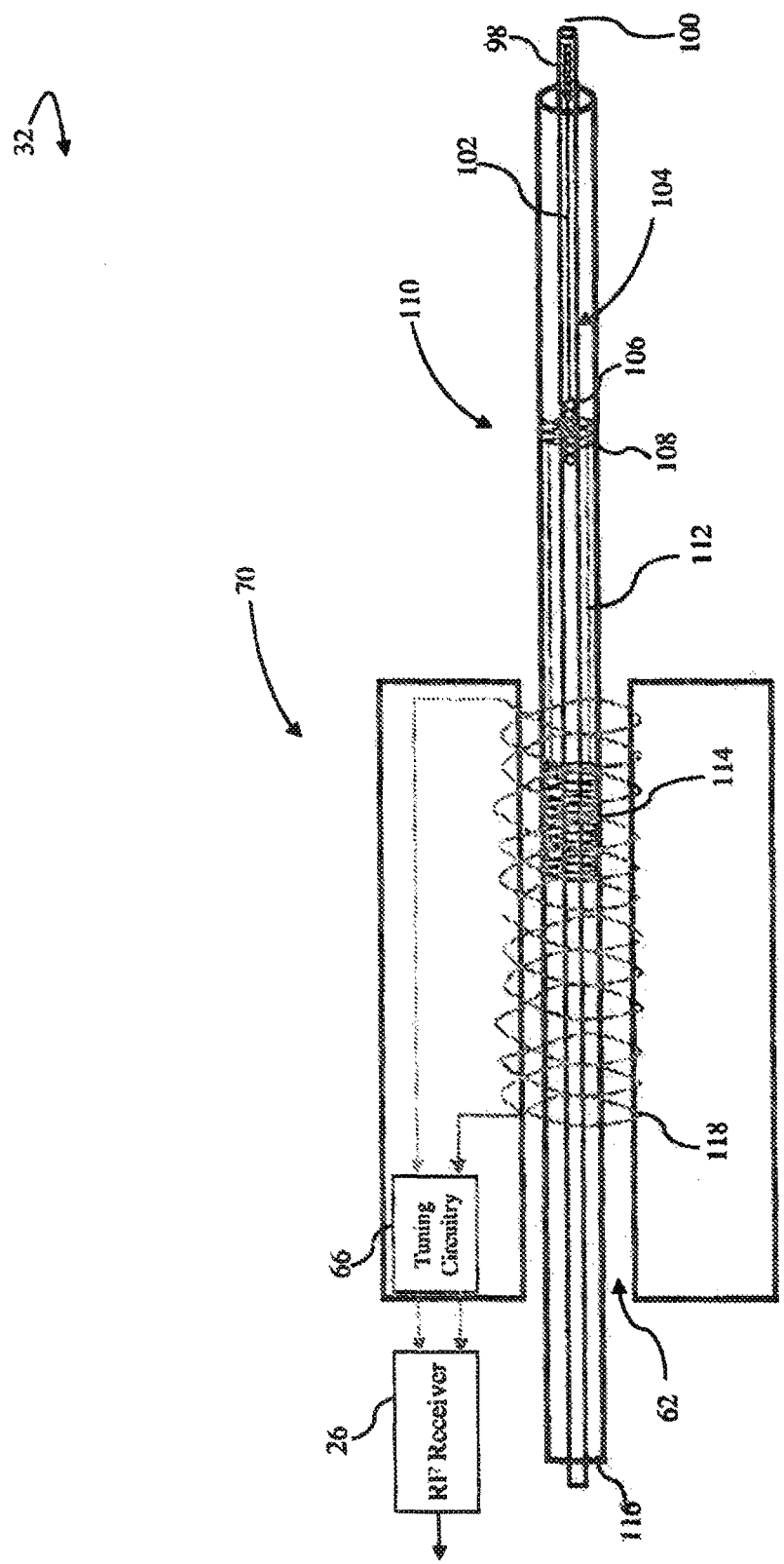
FIG. 4 is a diagrammatic side sectional view of an inductive handpiece inductively coupled to a catheter and then to a guide wire via a cascaded inductive coupling.

With reference to FIG. 4, an alternate configuration includes at least two cascaded inductive couplings which are incorporated into an interventional instrument comprising of a catheter and guidewire arrangement or a needle and needle-guide arrangement. An RF coil 98, disposed adjacent a distal end 100 is connected with a first transmission line 102 which extends the length of the interventional accessory or device 104 to an interventional accessory inductive winding 106. A first interventional instrument winding 108 is along an interventional instrument 110. The first interventional instrument winding 108 and the accessory winding 106 define a transformer which is tuned to pass RF signals at a particular frequency or band of frequencies. The first interventional instrument winding 108 is connected with a second transmission line 112 which extends the length of the interventional instrument 110 to second interventional instrument inductive winding 114 disposed near a proximal end 116 of the interventional instrument 110. A handpiece inductive coil 118 is disposed annularly along bore 62. The handpiece inductive coil 118 and the second interventional instrument inductive winding 114 define a second transformer which is tuned to pass RF signals at a particular frequency or band of frequencies. In this manner, the handpiece is inductively coupled to interventional accessory 104 via a series of inductive couplings in order to block the passage of direct current and other frequencies while permitting imaging, spectroscopy, localization, and the like. The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:
1. A handpiece comprising:
an interventional instrument;
an interventional accessory positioned within the interventional instrument and extending along a length of a interventional instrument;
a first transmission line positioned within the interventional accessory and extending along the length of a interventional accessory from an accessory winding to an RF coil at a distal end of the interventional accessory, an axial position of the accessory winding being selectively positionable by sliding the interventional accessory axially relative to a first interventional instrument winding of the interventional instrument;
an insulating support configured to be supported outside a subject during insertion of the interventional instrument in the subject, the insulating support having an internal bore for receiving the interventional instrument during the insertion of the interventional instrument in the subject, wherein the insulating support supports a portion of the interventional instrument which includes a second transmission line in, but spaced from, the internal bore of the insulating support; and
a handpiece inductive coil disposed along the internal bore, wherein the handpiece inductive coil interacts with the second transmission line to form an inductive coupling to the second transmission line,
wherein the second transmission line connects a second interventional instrument winding to the first interventional instrument winding, an axial position of the second interventional instrument winding being selectively positionable by sliding the interventional instrument axially relative to the handpiece inductive coil.

2. The handpiece according to claim 1, further including matching, amplification, and tuning circuitry.

3. The handpiece according to claim 1, wherein the second transmission line is rotatable and axially translatable with respect to the internal bore, and wherein the handpiece further includes a locking mechanism that selectively inhibits axial translation of the interventional instrument relative to the insulting support.

4. The handpiece according to claim 1, wherein:
the interventional instrument and the second transmission line are hermetically sealed; and
the second transmission line is flexible.

5. The handpiece according to claim 1, wherein the insulating support includes:
a locking ring configured to resiliently engage an array of adjacent annular channels of the interventional instrument.

6. The handpiece according to claim 1, wherein the insulating support includes:
a bushing in which the second transmission line is slidably received; a compressible element, which under action of a compression element, selectively presses the bushing into tighter frictional engagement with a portion of the interventional instrument that is received in the internal bore; and
bearing elements between the compressible element and the bushing to facilitate rotation of the bushing element and the interventional instrument relative to the handpiece when the compressible element has urged the bushing into tight engagement with the interventional instrument.

7. A magnetic resonance (MR) system comprising:
a magnet which generates a static magnetic field in an examination region;
a radio frequency transmit coil configured to induce magnetic resonance of a subject in the examination region;

a radio frequency receive coil configured to acquire magnetic resonance data from the examination region; and a handpiece with which an interventional instrument is adjustably positioned in the examination region, wherein the interventional instrument comprises an interventional accessory positioned within the interventional instrument and extending along a length of the interventional instrument, a first transmission line positioned within the interventional accessory and extending along a length of the interventional accessory from an accessory winding to an RF coil at a distal end of the interventional accessory, an axial position of the accessory winding being selectively positionable by sliding the interventional accessory axially relative to a first interventional instrument winding of the interventional instrument, and wherein the handpiece is configured to receive the interventional instrument and comprises:

an insulating support configured to be supported outside the subject during insertion of the interventional instrument in the subject, the insulating support having an internal bore for receiving the interventional instrument during the insertion of the interventional instrument in the subject, wherein the insulating support supports a portion of the interventional instrument which includes a second transmission line in, but spaced from, the internal bore of the insulating support; and a handpiece inductive coil disposed along the internal bore, wherein the handpiece inductive coil interacts with the second transmission line to form an inductive coupling to the second transmission line, wherein the second transmission line connects a second interventional instrument winding to the first interventional instrument winding, an axial position of the second interventional instrument winding being selectively positionable by sliding the interventional instrument axially relative to the handpiece inductive coil.

8. The magnetic resonance system according to claim 7, wherein the handpiece inductive coil is electrically connected with at least one of a radio frequency transmitter and a radio frequency receiver.

9. The magnetic resonance system according to claim 8, further including:

an MR data processor which processes data from the RF coil to produce one of magnetic resonance imaging data, magnetic resonance spectroscopy data, and interventional instrument coil locating information.

10. A method of operating a handpiece, the method comprising acts of:

providing an interventional instrument;

providing an interventional accessory positioned within the interventional instrument and extending along a length of the interventional instrument;

providing a first transmission line positioned within the interventional accessory and extending along a length of the interventional accessory from an accessory winding to an RF coil at a distal end of the interventional instrument, connecting the interventional instrument with an insulating support such that a second transmission line extending through the interventional instrument is supported in and spaced from a bore of the insulating support and axially slidable relative to the bore and rotatable relative to the bore;

supporting the insulating support outside a subject for insertion of the interventional instrument in the subject;

selectively positioning the accessory winding by sliding the interventional accessory axially relative to a first interventional instrument winding of the interventional instrument;

sliding the interventional instrument axially relative to the bore to adjust inductive coupling between a second interventional instrument winding connected with the second transmission line and a handpiece inductive coil to adjust coupling strength of the inductive coupling, wherein the handpiece inductive coil is disposed along the bore of the insulating support, wherein the second transmission line connects the second interventional instrument winding to the first interventional instrument winding; and locking the interventional instrument to inhibit axially sliding movement relative to the insulating support while permitting rotation of the interventional instrument relative to the isulating support.

11. The method according to claim 10, further including acts of:

inserting the interventional instrument into a subject disposed in an examination region of a magnetic resonance system;

during insertion of the interventional instrument, manually rotating the interventional instrument relative to the insulating support.

12. The method according to claim 10, wherein the handpiece inductive coil is connected with at least one of a radio frequency transmitter and a radio frequency receiver, the method further including an act of:

at least one of transmitting radio frequency signals with the distal coil and receiving radio frequency signals with the RF coil.

13. The method according to claim 12, further including an act of:

processing signals received from the RF coil to generate at least one of magnetic resonance image data, magnetic resonance spectroscopy data, and interventional instrument coil localization data.

* * * * *